United States Patent
Watanabe et al.

(10) Patent No.: US 7,662,799 B2
(45) Date of Patent: Feb. 16, 2010

(54) POWDER OF AMINO ACIDS AND METHOD FOR PRODUCING THE SAME

(75) Inventors: Aiji Watanabe, Kawasaki (JP); Junichi Katouno, Kawasaki (JP); Teruo Yoshida, Kawasaki (JP); Susumu Tsujimoto, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 12/168,566

(22) Filed: Jul. 7, 2008

(65) Prior Publication Data

US 2008/0275124 A1  Nov. 6, 2008

Related U.S. Application Data

(63) Continuation of application No. 10/921,895, filed on Aug. 20, 2004, now abandoned, which is a continuation of application No. PCT/JP03/01198, filed on Feb. 5, 2003.

(30) Foreign Application Priority Data

Feb. 22, 2002 (JP) ............... 2002-046580
Jul. 10, 2002 (JP) ............... 2002-201848

(51) Int. Cl.
  *A61K 31/175* (2006.01)
  *A61K 31/195* (2006.01)
  *A61K 9/50* (2006.01)
(52) U.S. Cl. ............ 514/53; 514/561; 424/499
(58) Field of Classification Search ......... 514/53, 514/561; 424/499
See application file for complete search history.

(56) References Cited

U.S. PATENT DOCUMENTS

| 2,797,080 | A | 6/1957 | Johnson et al. |
| 5,538,883 | A | 7/1996 | Nishimoto et al. |
| 5,854,846 | A | 8/1998 | Watanabe et al. |
| 6,254,889 | B1 | 7/2001 | Kigoshi et al. |
| 6,455,511 | B1 | 9/2002 | Kampinga et al. |
| 6,582,728 | B1 | 6/2003 | Platz et al. |
| 6,743,443 | B1 | 6/2004 | Furitsu et al. |
| 2001/0006939 | A1 | 7/2001 | Niven et al. |
| 2003/0202978 | A1 | 10/2003 | Maa et al. |
| 2004/0214746 | A1 | 10/2004 | Bosch et al. |
| 2005/0031769 | A1 | 2/2005 | Watanabe et al. |

FOREIGN PATENT DOCUMENTS

| JP | 06-227975 | 8/1994 |
| JP | 8-281155 | 10/1996 |
| JP | 2001-057851 | 3/2001 |
| WO | 97/23239 | 7/1997 |

OTHER PUBLICATIONS

Physical Pharmacy, 2<sup>nd</sup> edition, published 1969 by Leas & Febiger, (PA), pp. 527-528.

*Primary Examiner*—Raymond J Henley, III
(74) *Attorney, Agent, or Firm*—Oblon, Spivak, McClelland, Maier & Neustadt, L.L.P.

(57) ABSTRACT

Dry powders of amino acids which exhibit great oral meltability and solubility, may be produced by spray drying a hydrous liquid of amino acids to produce a powder of amino acids, where the hydrous liquid of amino acids is prepared into the form of microfine liquid droplets in the presence of trehalose for spray drying, to obtain a powder having a mean particle size of 0.1 µm to 15 µm, as well as granulating and drying during the spray drying or after the spray drying, to obtain a granulated powder having a mean particle size of 20 µm to 1,000 µm.

22 Claims, 1 Drawing Sheet

POWDER OF AMINO ACIDS AND METHOD FOR PRODUCING THE SAME

CROSS REFERENCES TO RELATED APPLICATIONS

This application is a continuation of U.S. Ser. No. 10/921,895, filed on Aug. 20, 2004 now abandoned, which is a continuation of International Patent Application No. PCT/JP03/01198, filed on Feb. 5, 2003, and claims priority to Japanese Patent Application No. 046580/2002, filed on Feb. 22, 2002, and Japanese Patent Application No. 201848/2002, filed on Jul. 10, 2002, all of which are incorporated herein by reference in their entireties.

BACKGROUND OF THE INVENTION

1. Field of the Invention

The present invention relates to powders of amino acids, which is a microfine or granulated amino acid powder containing trehalose. The present invention further relates to methods for producing such powders.

2. Discussion of the Background

Amino acids, amino acid salts, and amino acid derivatives (simply referred to as amino acids hereinafter) are widely used in medical diets for nutrition supplements, disease-specific amino acid preparations for oral administration and infusion for subject patients with renal impairment and liver disorders, infantile nutritious compositions, diet food materials, health foods, and functional foods. Further, amino acids are used in cosmetics and in veterinary preparations for dosing to animals, after being mixed in feeds and the like.

Trehalose, when contained in amino acids, not only serves as a saccharide nutrient but also suppresses the bittern taste of amino acids, advantageously, without any occurrence of the Maillard reaction (browning reaction). Therefore, the presence of trehalose therein is recommended. Specifically, those formulations described below are known.

For example, trehalose-coated (film) powders of amino acids are known, and may be prepared by one of the following methods. In a first method, a binder is added to a powder of amino acids in mixture to prepare granules by an extrusion granulation process, and the granules surfaces are then coated with trehalose as a coating material by fluid granulation. In a second method, trehalose and a binder are added to a powder of amino acids in mixture for coating by fluid granulation, and spraying an aqueous ethanol solution over the resulting coated powder for granulation (see, JP-A-6-227975).

Furthermore, an amino acid infusion containing trehalose and having the same effects as described above is also known (see, JP-A-6-70718).

Also known are amino acid food products containing trehalose, which are adjusted to a pH 3.0 to 6.0 by the addition of sour agents such as citric acid so as to prevent flavor deterioration due to heating of the amino acid, or flavor modification or color modification of the amino acid during long-term storage. The test results of heating the hydrous amino acid-containing solution are disclosed (see, JP-A-2000-4836).

As compositions for use in the suppression of blood amino acid variation following vigorous athletic motion, a hydrous solution of a composition of amino acids and sugar is disclosed, which contains at least 13 types of amino acids and trehalose. The hydrous solution is said to be effective for the improvement of athletic potential and the amelioration of fatigue (see, JP-A-2000-72669).

As described above, various findings exist about amino acid compositions containing trehalose, but only JP-A-6-227975 describes such a powder. Further, no amino acid powder with a high oral meltability, high solubility, and masked taste is known. In particularly, there remains a need for a dry power of a branched amino acid and a slightly soluble amino acid, which has improved oral meltability and solubility and suppressed bitterness.

As production methods of dry powders, meanwhile, the spray drying method, hot-air drying method, and freeze-drying method are known. Among them, the spray drying method is capable of producing microfine particles, and is a dry method for recovering a dry powder of spherical and spherical shell-shaped powder, by dispersing a solution or a particle slurry into the form of microfine particles in hot air, where the spray method uses pressure nozzle, rotating disk, and two-fluid nozzle and the like. In many cases, the mean particle size of the dry powder is about 20 μm to 500 μm (see, Handbook of Chemistry and Engineering, revised sixth edition, p. 770, p. 780 (1999), issued by Maruzen), while in the pharmaceutical field, a production example of microfine particles of 10 μm or less is introduced (see, JP-A-9-235238, JP-T-10-500672, and JP-A-11-114027). In recent years, a four-fluid nozzle has been developed, which has enabled mass-scale spray drying with a liquid droplet having a mean particle size of several micrometers (see, Chemical Apparatus, pp. 60-65 (June, 2000), and Japanese Patent No. 2,797,080, and JP-A-2002-17337, etc.).

Similar to the powders containing microfine amino acids, an inhalation dry composition containing the pharmacologically active component, interferon, as the essential component and containing a hydrophobic amino acid selected from leucine, isoleucine, and valine at 60% or more to less than 100% (mean particle size (volume-based distribution) of 0.1 μm or more to 10 μm or less) is disclosed for the purpose of avoiding the deliquescence of the inhalation dry composition, when left at a high humidity (see, JP-A-9-235238). In Example 2 of JP-A-9-235238, a dry particle powder is obtained as a control, by preparing a solution containing 3.5 g of isoleucine, 0.7 g of serum albumin, 695.8 g of deionized water, and 300 g of ethanol for spray drying, and then spraying the resulting solution with a spray dryer (aerodynamic mean particle size of 0.9897 μm). However, this Example does not include any description of oral meltability, solubility, and taste masking.

Moreover, it is also desired that the production of powders of amino acids by spray drying in such manner can be done on a mass scale; that the quality can be maintained; and that the oral meltability and solubility of the resulting powders are great. Accordingly, there remains a need for any improved process so as to satisfy these properties.

SUMMARY OF THE INVENTION

Accordingly, it is one object of the present invention to provide novel dry powders (meaning microfine powder or granulated powder) of amino acids, which have great oral meltability and solubility and a high masking effect of the taste.

It is another object of the present invention to provide novel methods for preparing such powders.

It is another object of the present invention to provide novel spray drying methods for preparing such powders.

These and other objects, which will become apparent during the following detailed description, have been achieved by the inventors' discovery that a dry powder of amino acids with great oral meltability and solubility can be produced by a spray dryer capable of preparing an amino acid solution containing trehalose into the form of liquid droplets of several micrometers (particle). Thus, the invention has been achieved and provides the following embodiments:

(1) A method for producing a powder of amino acids, comprising spray drying a hydrous liquid of amino acids to produce a powder of amino acids, where the hydrous liquid of amino acids is prepared into the form of microfine liquid droplets in the presence of trehalose for spray drying to prepare a powder having a mean particle size (Mean Volume Diameter) of 0.1 μm to 15 μm.

(2) A method for producing a powder of amino acids, comprising spray drying a hydrous liquid of amino acids to produce a powder of amino acids, where the hydrous liquid of amino acids is prepared into the form of microfine liquid droplets in the presence of trehalose for spray drying, and the resulting powder is then granulated and dried during spray drying or after spray drying, to prepare a granulated powder having a mean particle size (Mean Volume Diameter) of 20 μm to 1,000 μm.

(3) A method for producing a powder of amino acids as described in (1) or (2), where the trehalose is added to the hydrous liquid of amino acids or the trehalose is prepared in the form of a trehalose solution at a microfine liquid droplet state to be fed into a spray dryer and/or a granulation dryer.

(4) A method for producing a powder of amino acids as described in (1) through (3), where the exhaust gas temperature during spray drying or granulation drying is less than 97° C.

(5) A method for producing a powder of amino acids as described in (1) through (4), where the amino acids are slightly soluble amino acids.

(6) A method for producing a powder of amino acids as described in (5), where the amino acids are branched amino acids.

(7) A powder of amino acids, as obtained in a manner described in (1) through (6).

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein.

DETAILED DESCRIPTION OF THE PREFERRED EMBODIMENTS

Figure 1:
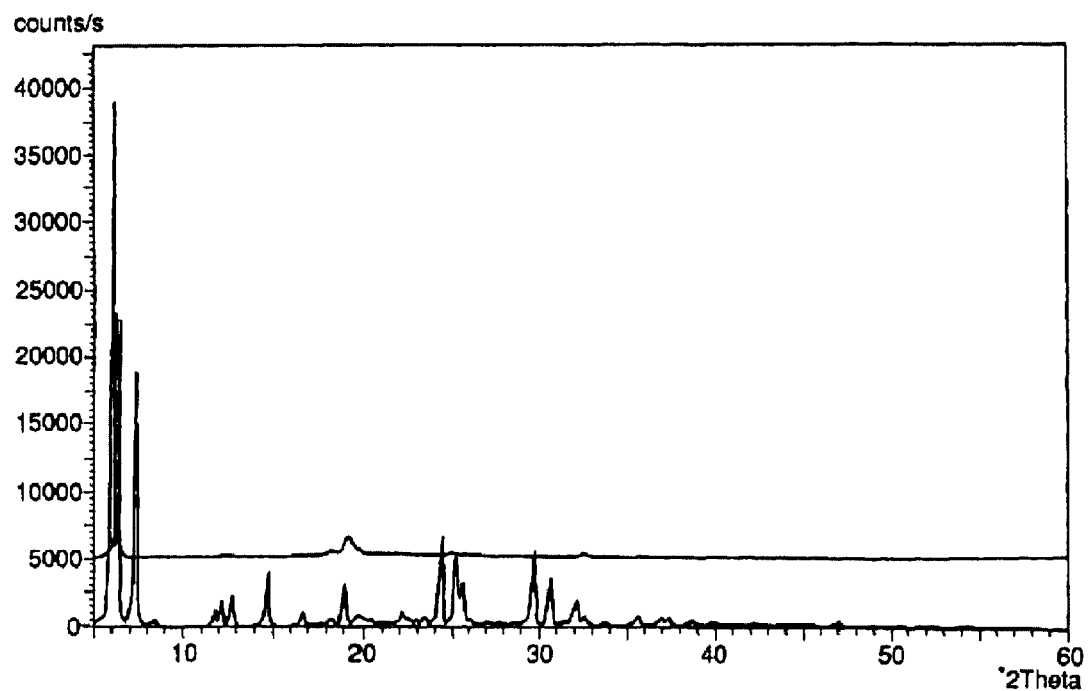
FIG. 1 depicts two X-ray diffraction charts, in which the upper line is the X-ray powder diffraction pattern of the spray dry granulated powder of Example 1 and the lower line is the X-ray powder diffraction pattern of the mixed powder before drying of Comparative Example 2.

Thus, in a first embodiment, the present invention provides novel powders comprising amino acids and methods of producing such powders. The various aspects of the present invention are specifically described below.

Amino Acids:

The amino acids to be used in accordance with the present invention include amino acids, salts of amino acid, and amino acid derivatives, for example branched amino acids such as leucine, isoleucine, and valine, sulfur-containing amino acids such as cystine and methionine, aromatic amino acids such as phenylalanine and tyrosine, heterocyclic amino acids such as tryptophan and histidine, acidic amino acids such as aspartic acid and glutamic acid, and various amino acid derivatives such as sulfur-containing amino acid derivatives including taurine. These amino acids may be used singly or in combination of two or more thereof.

The subject hydrous solution of the amino acid(s) is in the solution state or a particle slurry solution state (for example, a slurry containing particles having a mean particle size (Mean Volume Diameter) of 0.1 μm to 15 μm), and the solvent may contain ethyl alcohol and the like.

The amino acids to which the present invention is effectively applied include amino acids relatively slightly soluble in water, such as amino acids with a solubility of 9 g or less in 100 g of water at 20° C. Particularly, the amino acids preferable for the application of the present invention are slightly soluble amino acids. The present invention is preferably applied to amino acids with a solubility of 5 g or less in 100 g of water at 20° C. The present invention is applicable to leucine, isoleucine, cystine, phenylalanine, tyrosine, tryptophan, and aspartic acid, and salts thereof and derivatives thereof, in particular.

The amount of the amino acid(s) to be used generally includes but is not specifically limited to 20% by weight to 95% by weight in the dry powder. If necessary, the amount may be at 50% by weight to 95% by weight, 60% by weight to 95% by weight, or 70% by weight to 95% by weight. The amount to be used may satisfactorily be determined, taking account of the conditions of product design, namely the balance between the amount of amino acid(s) required as effective ingredients and the specific volume of the dry powder of amino acids.

Trehalose:

The raw material trehalose for use in accordance with the invention includes α,α-trehalose, α,β-trehalose, and β,β-trehalose. α,α-Trehalose is preferable, because α,α-trehalose is a naturally occurring substance and is now not costly. If necessary, the dihydrate thereof with almost no hygroscopicity over time may be used, satisfactorily. For example, a commercially available "Treha" (Hayashibara, Co., Ltd.) is listed and may be used.

The amount of trehalose (on an anhydride basis) is 5% by weight to 80% by weight in the dry powder, satisfactorily. If necessary, the content can be 5% by weight to 50% by weight, 5% by weight to 40% by weight and 5% by weight to 30% by weight. The amount of trehalose to be used may be adjusted to the conditions for product design, as described above.

The trehalose and the amino acid(s) may be mixed together to prepare a mixture solution prior to spray drying. Otherwise, a hydrous solution containing the amino acid(s) as the main components and a hydrous solution containing trehalose as the main component may be simultaneously sprayed together during spray drying. Alternatively, after a hydrous solution containing the amino acid(s) as the main component(s) has been spray dried, a hydrous solution containing trehalose as the main component may be sprayed and/or granulated as a coating agent and a binder, satisfactorily. If necessary, further additives, other than trehalose, may be added satisfactorily as a matter of course.

Apparatus in Relation with Spray Drying:

As the spray drying apparatus for use in accordance with the present invention, commercially available apparatus can be used. For example, a spray drying apparatus which has a vertical parallel flow function is preferable. In particular, when a system with a dehumidifying and drying function is used, the productivity can be maintained, even under drying conditions with dehumidification at low temperature, and the quality of the resulting dry powder can be maintained at a high level, preferably. As described below, for example, an apparatus capable of blowing a high volume of dry dehumidified gas at 1% RH or less is particularly preferable as the dehumidifying apparatus, which is for example a dry dehumidifier BX series manufactured by Munsters K.K., and HCS series and HCP series manufactured by Nichias Corporation. Other suitable spray drying apparatus include the micromist dryer MD series and the hybrid granulator series manufactured by Fujisaki Electric Co., Ltd., the FSD spray dryer with internal fluid layer as manufactured by Niro Corporation, the fluid granulation spray dryer and L-8 type spray dryer manufactured by O-gawara Chemical Engineering Machine Corporation, and the DL-21 type and GB-21 type manufactured by Yamato Scientific Co., Ltd.

In accordance with the present invention, it is important to carry out the spray drying, using a spray nozzle capable of generating a liquid droplet (microfine particle, single particle) having a mean particle size (Mean Volume Diameter) of 0.1 µm or more to less than 20 µm. Specifically, it is important to carry out the drying using a spray dryer or a spray dry granulation apparatus with a spray nozzle capable of generating a large volume of liquid droplets having a mean particle size (Mean Volume Diameter) of 0.1 µm or more to less than 20 µm, preferably 0.1 µm to 10 µm, and more preferably 1 µm to 8 µm. When the liquid droplet is dried, a dry powder having a mean particle size (Mean Volume Diameter) of 0.1 µm to 15 µm, preferably 0.1 µm to 7 µm, and more preferably 0.7 µm to 6 µm is obtained. This is preferable with the respect to the control of the product quality and productivity, because such liquid droplets can be dried under low-temperature conditions within a short time. For example, the four-fluid nozzle manufactured by Fujisaki Electric Co., Ltd., which can spray a large volume (for example, 1 kg/mm) of liquid droplets of several micrometers (see, Japanese Patent No. 2,797,080; Chemical Apparatus, 2000, No. 6, pp. 60-65) and the three-fluid nozzle manufactured by Fukusen Production Corporation, which can spray a large volume (for example, 150 g/min) of liquid droplets of 1 µm to 10 µm (see, Japanese Patent Publication Sho 63-5146) are included. The four-fluid nozzle is particularly preferable because a large volume can be sprayed from the nozzle.

Granulation:

Furthermore, the spray dryer is preferably an apparatus with a granulation function or is additionally mounted with a granulation dryer if the spray dryer does not have such granulation function (referred to as "spray dry granulation apparatus"). Then, importantly, the resulting apparatus is of a specification to enable the granulated powder (aggregate particle powder) to be finally dried to the desired moisture. In the case of particles with such a small specific gravity such as those of amino acids for use in accordance with the present invention, particles (Mean Volume Diameter) of 0.1 µm to 15 µm disadvantageously involve difficulty in handling. Therefore, preferably, a granulation dryer is additionally mounted in the inside of the spray dryer or in a state in communication with the spray dryer.

Appropriate conditions for the granulation size may satisfactorily be selected, depending on the need. For example, the granulation size is 20 µm to 1,000 µm, and preferably 20 µm to 500 µm (Mean Volume Diameter). Satisfactorily, granulation is sometimes effected almost simultaneously with spray drying or in other cases, fluid granulation is effected after spray drying or both fluid granulation and spray drying are effected simultaneously.

Then, preferably, the apparatus can carry out the final drying during granulation or immediately after granulation. As to the conditions prior to or after granulation, the conditions such as the outlet temperature (also referred to as "drying temperature" or "exhaust gas temperature") of the spray dry granulation apparatus, the inlet temperature thereof, the outlet relative humidity thereof and the inlet relative humidity thereof are almost identical to those of spray drying conditions described below. In other words, the outlet temperature of the spray dry granulation apparatus is 20° C. to less than 97° C., preferably 20 to 80° C., and more preferably 20 to 60° C. Additionally, the outlet relative humidity of the spray dry granulation apparatus is 1% RH to 50% RH, preferably 3% RH to 35% RH, and more preferably 6% RH to 30% RH. Further, the inlet temperature of the spray dry granulation apparatus is 60 to 300° C., and preferably 70 to 180° C. Under conditions lower than 60° C., the productivity is undesirably lowered. Under conditions above 300° C., the quality of the resulting dry powder is undesirably deteriorated. Furthermore, the inlet relative humidity of the spray dry granulation apparatus of the invention is 35% RH or less, preferably 15% RH or less, more preferably 7% RH or less, and most preferably 1% RH or less. These preferable conditions are selected with the respect to the control of product quality such as the suppression of the Maillard reaction and with the respect to productivity improvement. Spray drying granulation apparatus with such granulation function include for example the "Hybrid Granulator Series as granulation apparatus on filter cloth with spray drying function equipped" manufactured by Fujisaki Electric Co., Ltd.

Operation Conditions of the Spray Dryer:

Among the operation conditions of the spray dryer, the outlet temperature (also referred to as "drying temperature" or "exhaust gas temperature") of the spray dryer is 20° C. to less than 97° C., preferably 20 to 80° C., and more preferably 20 to 60° C. At temperatures lower than 20° C., the productivity is undesirably lowered. Furthermore because the melting point of trehalose in the dihydrate form is 97° C., the outlet temperature is preferably set within a range not exceeding the melting point, with respect to quality control.

Meanwhile, the outlet relative humidity of the spray dryer set in the present invention is 1% RH to 50% RH, preferably 1% RH to 35% RH, and more preferably 1% RH to 30% RH. The outlet relative humidity of the spray dryer as referred to in accordance with the present invention means the relative humidity in the vicinity of the powder collection part of the spray dryer. For the spray dryer of the vertical parallel flow type, the outlet relative humidity (exhaust gas humidity) means the relative humidity at the exhaust part thereof. For the "Hybrid Granulator Series HGL-130 as granulation apparatus on filter cloth with spray drying function equipped" manufactured by Fujisaki Electric Co., Ltd., for example, the outlet relative humidity means the relative humidity (exhaust gas humidity) in the vicinity of the filter cloth at the powder collection part of the apparatus.

Herein, the inlet temperature of the spray dryer is 60 to 300° C., and preferably 70 to 180° C. Under conditions lower than 60° C., the productivity is undesirably lowered. Under conditions above 300° C., the quality of the resulting dry powder is undesirably deteriorated. Furthermore, the inlet relative humidity of the spray dryer of the present invention is 35% RH or less, preferably 15% RH or less, more preferably 7% RH or less, and most preferably 1% RH or less. These preferable conditions for the inlet temperature, the outlet temperature, the inlet relative humidity, and the outlet relative humidity are selected with the respect to the control of product quality such as the suppression of the Maillard reaction, and with respect to productivity improvement.

The volume of dry gas, for example dry air for use in accordance with the present invention is preferably 0.5 m/min or more, more preferably 1 m/min to 5 m/min, and still more preferably 1 m/min to 3.5 m/min, with respect to the improvement of the productivity of the dry powder. Herein, the volume of dry air means the air rate (m/min) in the spray dryer or at the cylinder part (the trunk part) of the body of the spray dry granulation apparatus. For the "Hybrid Granulator HGL-130 as granulation apparatus on filter cloth with spray drying function equipped" manufactured by Fujisaki Electric Co., Ltd., for example, the volume means the filtration rate. Further, the liquid transfer rate of the raw material solutions such as the hydrous solution of amino acids and the hydrous trehalose solution can be preset appropriately, in relation with the inlet temperature, the outlet temperature, the exhaust gas humidity, the types of the raw material solutions, the desired particle size and the like. Additionally, the spraying pressure is preferably 0.5 kg/cm$^2$ or more, more preferably 1 kg/cm$^2$ to 5 kg/cm$^2$, and still more preferably 1 kg/cm$^2$ to 3 kg/cm$^2$.

Furthermore, the gas to be used in accordance with the invention is preferably air, but may be a gas other than air, depending on the case. Inert gases, for example nitrogen gas and carbonate gas, can be used. In the case of addition of readily oxidizable substances or readily modifiable substances, the use of an inert gas is effective and may be preferred.

The moisture content (loss on drying) of the dry powder thus produced is preferably 5 wt. % or less when dried at 60° C. for 5 hours. By spray drying the hydrous solution containing trehalose and amino acids or the hydrous solution containing amino acids and the hydrous solution containing trehalose in the form of liquid droplets having a mean particle size of 0.1 μm or more to less than 20 μm, and preferably 0.1 μm to 10 μm, the liquid droplet is instantly dried. By instant drying at a temperature lower than 97° C., and preferably at a temperature of 20 to 60° C., the trehalose in the dry powder exists in a structure of an almost amorphous state. The existence in the amorphous state may possibly generate excellent effects such as oral meltability of the dry powder, the solubility thereof, and the taste-masking effect thereof. Furthermore, some of amino acids are observed to have low crystallinity, according to the method of the present invention, which suggests an increase of amorphous materials.

The dry powder thus produced can be used as it is or as an intermediate material, in the pharmaceutical field of, for example, oral or infusion amino acid preparations specific to individual diseases for subject patients with renal impairment or liver disorders, and the cosmetic field, and the like. For example, the dry powder can be used in the form of powders, tablets, and capsules, as individual materials for foods such as sport drinks, diet food materials, health foods and functional foods, and amino acid-series cosmetics.

Other features of the invention will become apparent in the course of the following descriptions of exemplary embodiments which are given for illustration of the invention and are not intended to be limiting thereof.

EXAMPLES

Herein, the mean particle size of the microfine powders (single particle powder generated from liquid droplet) were measured visually with a microscope, while the mean particle size (Mean Volume Diameter) of the granulated powders were measured with a dry particle size distribution measurement system of laser diffraction & scattering microtruck, 9320 HRA manufactured by Honeywell Co., Ltd.).

Example 1

Water was added to 4.98% by weight of a mixture of branched amino acids having a mean particle size (Mean Volume Diameter) of 20 μm (leucine:isoleucine valine=47% by weight:24% by weight:29% by weight; manufactured by Ajinomoto Co.); 4.98% by weight trehalose dihydrate ("Treha" manufactured by Hayashibara, Co., Ltd.); 0.45% by weight of hydroxypropyl cellulose; and others, to prepare an aqueous solution of amino acids at a solid concentration of 10.4% by weight.

The flow of dehumidified hot air having a relative humidity of 1% RH at 25° C. (produced by the dry dehumidifier BX-600 type manufactured by Munsters, K.K.) was preset to 5.5 m$^3$/min (filtration rate of about 3 m/min), and spray drying and granulation were carried out with a "HGL-130 type as granulation apparatus on filter cloth with spray drying function equipped" manufactured by Fujisaki Electric Co., Ltd. using the conditions of the inlet temperature of the spray dry granulation apparatus described below as set to 131 to 139° C. and the feed rate of the aqueous solution of amino acids as set to 6.7 to 7.3 kg/hr. With the exhaust gas temperature (outlet temperature) at 49 to 58° C. and the exhaust gas humidity (outlet relative humidity) at 20% RH to 30% RH, the mean particle size of the microfine powder (single particle powder generated from the liquid droplets) was about 2 μm to 3 μm (diameter), as observed with a microscope. Then, the microfine powder was densified under pressure into granules on the filter membrane for particle collection, so that the dry powder granulated as the final product was a powder of amino acids, which had a mean particle size (Mean Volume Diameter) of 40 μm (moisture content of 4 wt. %).

Comparative Example 1

An aqueous solution of amino acids (a solid concentration of 5.85% by weight) was prepared at ratios of 4.95% by weight of a powder of branched amino acids of a mean particle size (Mean Volume Diameter) of 20 μm (leucine:isoleucine:valine=47% by weight:24% by weight:29% by weight; manufactured by Ajinomoto Co.); 0.45% by weight of sucrose powder; 0.45% by weight of hydroxypropyl cellulose; and 94.15% by weight of water.

The flow of dehumidified hot air having a relative humidity of 1% RH at 25° C. (produced by the dry dehumidifier BX-600 type manufactured by Munsters K.K.) was preset to 5.5 m$^3$/min (filtration rate of about 3 m/min), and spray drying and granulation were carried out with a "HGL-130 type as granulation apparatus on filter cloth with spray drying function equipped" manufactured by Fujisaki Electric Co., Ltd., using the conditions of the inlet temperature of the spray dry granulation apparatus described below set to 130 to 137° C., and the supply rate of aqueous amino acids solution set to 6.1 to 7.7 kg/hr. With the exhaust gas temperature (outlet temperature) at 49 to 61° C. and the exhaust gas humidity (outlet relative humidity) at 18% RH to 30% RH, the mean particle size (diameter) of the microfine powder (single particle powder generated from the liquid droplets) was about 2 μm to 3 μm, as observed with a microscope. Then, the microfine powder was densified under pressure into granules on the filter membrane for particle collection, so that the dry powder granulated as the final product was a powder of amino acids, which had a mean particle size (Mean Volume Diameter) of 32 μm (moisture content of 1 wt. %).

Comparative Example 2

Leucine, isoleucine, and valine (manufactured by Ajinomoto Co.) were individually pulverized to a mean particle size (Mean Volume Diameter) of 20 μm, and were then mixed together uniformly at 47% by weight, 24% by weight and 29% by weight, respectively. Then, 47.8% by weight of the powder of the amino acid mixture, 47.8% by weight of trehalose•dihydrate ("Treha" manufactured by Hayashibara, Co., Ltd.), and 4.4% by weight of hydroxypropyl cellulose powder were uniformly mixed together.

Test Example 1

The granulated powder samples or powder mixture samples as recovered in Example 1, and Comparative Examples 1 and 2 were evaluated for their oral meltability, solubility, the degree of bitterness, and solidification property. The results are shown in Table 1.

TABLE 1

| | Evaluation results | | |
|---|---|---|---|
| Items | Example 1 | Comparative Example 1 | Comparative Example 2 |
| Oral meltability | 5 | 2 | 3 |
| Bitterness masking | 5 | 2 | 3 |
| Solubility | 5.5 min | 6.00 min | 14 min |
| Solidification | no problem | no problem | no problem |

Notes:
The oral meltability and the degree of bitterness masking were evaluated, while the scores of those of Comparative Example 2 were ranked as 3.
1. Oral meltability (5: very good; 4: relatively good; 3: normal; 2: slightly poor; 1: poor)
2. Degree of bitterness masking (5: very good; 4: relatively good; 3: normal; 2: slightly poor; 1: poor)
3. Solubility: 250 ml of water at 16° C. was placed in a 300-ml beaker; an amount of a sample was measured to an amino acid content of 50 mg, and was then placed in the beaker under agitation at 300 rpm with a magnetic stirrer, F-616 Type (Tokyo Glass Kikai, Co., Ltd.), the time until the sample was completely dissolved was determined and is reported.
4. Solidification property: After individual samples were prepared, the samples were pouched and sealed, and were then left to stand for 2 weeks, to observe the solidified state.

As described above, the granulated powder containing trehalose (Example 1) had great oral meltability, great solubility, and a great effect on bitterness masking. The granulated powder containing sugar (Comparative Example 1) had good solubility but poor oral meltability without any masking effect of bitterness. Additionally, the granulated powder tasted very powdery and had bad aftertaste.

Herein, the spray dry granulated powder containing trehalose (Example 1) is compared with the mixed powder of the powders and of the same composition (Comparative Example 2). The solubility of the mixed powder of the powders of Comparative Example 2 was similar to the solubility (13.5 minutes) of the "mix powder of amino acids" (leucine:isoleucine:valine=47% by weight:24% by weight:29% by weight) as the raw material of Comparative Example 2 but was apparently poorer than the solubility of the spray dry granulated powder containing trehalose (Example 1). Furthermore, the oral meltability and the bitterness-masking effect of the mix powder of the powders of Comparative Example 2 were more or less worse than those of the spray dry granulated powder (Example 1).

Test Example 2

Figure 2:
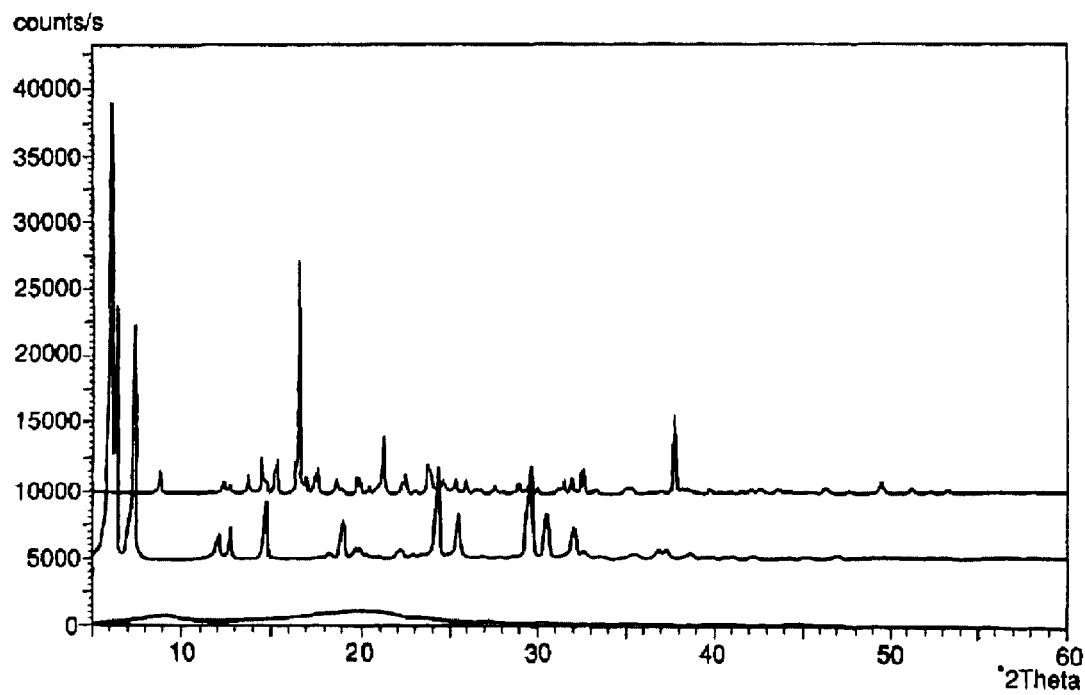
FIG. 2 depicts three X-ray diffraction charts, in which the upper line is the X-ray diffraction pattern of trehalose; the middle line is the X-ray diffraction pattern of "the mix powder of amino acids" used as the raw materials of Comparative Example 2; and the lower line is the X-ray diffraction pattern of hydroxypropyl cellulose.

The spray dry granulated powder containing trehalose (Example 1), the mixed powder of the powders (Comparative Example 2) and the individual raw material powders such as trehalose were analyzed by powder X ray diffraction. The results are shown in FIGS. 1 and 2. It was clearly verified that trehalose in the spray dry granulated powder of Example 1 was in an amorphous state, which apparently makes contributions to the oral meltability and the bitterness-masking effect. Additionally, the spray dry granulated powder (Example 1) lost the crystallinity essential to amino acids. The spray dry granulated powder (Example 1) exhibits partial crystallinity, but contains an amorphous fraction at a high content, when compared with Comparative Example 2.

In accordance with the present invention, a dry powder of amino acids of high quality, such as improved oral meltability, solubility, and a taste-masking effect, can be obtained.

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

What we claim is:

1. A method for producing a dry powder, said method comprising:
    spray drying a hydrous liquid comprising at least one amino acid in the presence of trehalose into the form of liquid droplets to obtain a dry powder in a spray dryer,
    wherein said dry powder has a mean particle size of 0.1 μm to 15 μm, and
    wherein the amount of said at least one amino acid ranges from 20% by weight to 95% by weight in the dry powder and the amount of trehalose, on an anhydride basis, is 5% by weight to 80% by weight in the dry powder.

2. The method of claim 1, wherein said trehalose is added to said hydrous liquid comprising said at least one amino acid.

3. The method of claim 1, wherein said trehalose is prepared into the form of a trehalose solution existing as liquid droplets and is spray dried with said hydrous liquid comprising said at least one amino acid.

4. The method of claim 1, wherein said spray drying is carried out under a condition of an exhaust gas temperature during spray drying of less than 97° C.

5. A dry powder, wherein said powder is prepared by a process according to claim 1.

6. A method for producing a dry powder, said method comprising:
    spray drying a hydrous liquid comprising at least one amino acid in the presence of trehalose into the form of liquid droplets to obtain a spray dry powder in a spray dryer,
    granulating said spray dry powder either during or after said spray drying, to obtain a granulated powder, and drying said granulated powder to obtain a dry powder,
    wherein said dry powder has a mean particle size of 20 μm to 1,000 μm, and
    wherein the amount of said at least one amino acid ranges from 20% by weight to 95% by weight in the dry powder and the amount of trehalose, on an anhydride basis, is 5% by weight to 80% by weight in the dry powder.

7. The method of claim 6, wherein said trehalose is added to said hydrous liquid comprising at least one amino acid.

8. The method of claim 6, wherein said trehalose is prepared into the form of a trehalose solution existing as liquid droplets and is spray dried and/or a granulated with said hydrous liquid comprising said at least one amino acid.

9. The method of claim 6, wherein said spray drying or granulation is carried out under a condition of an exhaust gas temperature during spray drying of less than 97° C.

10. A dry powder, wherein said powder is prepared by a process according to claim 6.

11. The method of claim 1, wherein said spray dryer has an inlet relative humidity of 35% RH or less.

12. The method of claim 11, wherein said spray dryer has an outlet relative humidity of 1% RH to 50% RH.

13. The method of claim 12, wherein said spray dryer has an outlet temperature of 20 to 97° C.

14. The method of claim 6, wherein said spray dryer has an inlet relative humidity of 35% RH or less.

15. The method of claim 14, wherein said spray dryer has an outlet relative humidity of 1% RH to 50% RH.

16. The method of claim 15, wherein said spray dryer has an outlet temperature of 20 to 97° C.

17. The dry powder of claim 5, wherein said at least one amino acid is one or more amino acids having solubility of 9 g or less in 100 g of water at 20° C.

18. The dry powder of claim 5, wherein said at least one amino acid is one or more branched amino acids.

19. The dry powder of claim 5, wherein said at least one amino acid is a mixture of leucine, isoleucine and valine.

20. The dry powder of claim 10, wherein said at least one amino acid is one or more amino acids having solubility of 9 g or less in 100 g of water at 20° C.

21. The dry powder of claim 10, wherein said at least one amino acid is one or more branched amino acids.

22. The dry powder of claim 10, wherein said at least one amino acid is a mixture of leucine, isoleucine and valine.

* * * * *